(12) United States Patent
Vora et al.

(10) Patent No.: US 7,803,330 B2
(45) Date of Patent: Sep. 28, 2010

(54) PROCESS FOR ENHANCED OLEFIN PRODUCTION

(75) Inventors: Bipin V. Vora, Naperville, IL (US);
Peter R. Pujado, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 439 days.

(21) Appl. No.: 11/874,448

(22) Filed: Oct. 18, 2007

(65) Prior Publication Data

US 2008/0039667 A1 Feb. 14, 2008

Related U.S. Application Data

(62) Division of application No. 10/302,258, filed on Nov. 21, 2002, now Pat. No. 7,317,133.

(51) Int. Cl.
*B01J 8/04* (2006.01)

(52) U.S. Cl. .................. 422/190; 422/139; 422/189; 585/314; 585/315; 585/324; 585/325; 585/639; 585/640

(58) Field of Classification Search .................. 422/139, 422/189, 190; 585/314, 315, 324, 325, 639, 585/640
See application file for complete search history.

(56) References Cited

U.S. PATENT DOCUMENTS

| 3,485,890 | A | * | 12/1969 | Dixon | 585/251 |
| 5,026,935 | A | * | 6/1991 | Leyshon et al. | 585/315 |
| 5,914,433 | A | * | 6/1999 | Marker | 585/313 |
| 6,005,150 | A | * | 12/1999 | Vora | 585/324 |
| 6,049,017 | A | * | 4/2000 | Vora et al. | 585/324 |
| 6,156,947 | A | * | 12/2000 | Vora | 585/324 |
| 6,303,839 | B1 | * | 10/2001 | Marker | 585/313 |
| 2004/0102667 | A1 | * | 5/2004 | Vora et al. | 585/324 |

* cited by examiner

*Primary Examiner*—Walter D Griffin
*Assistant Examiner*—Huy-Tram Nguyen
(74) *Attorney, Agent, or Firm*—Mark Goldberg

(57) ABSTRACT

The present invention relates to a process for the production of light weight olefins comprising olefins having from 2 to 3 carbon atoms per molecule from an oxygenate feedstock. The process comprises passing the oxygenate feedstock to an oxygenate conversion zone containing a metal aluminophosphate catalyst to produce a light weight olefin stream. A propylene stream and/or mixed butylene is fractionated from said light weight olefin stream and a medium weight $C_4$ to $C_7$ stream is cracked in a separate olefin cracking reactor to enhance the yield of ethylene and propylene products.

8 Claims, 2 Drawing Sheets

PROCESS FOR ENHANCED OLEFIN PRODUCTION

CROSS-REFERENCE TO RELATED APPLICATION

This application is a Division of application Ser. No. 10/302,258, now U.S. Pat. No. 7,317,133, filed Nov. 21, 2002, the contents of which are hereby incorporated by reference in its entirely.

FIELD OF THE INVENTION

This invention relates to a process for the production of light weight olefins from an oxygenate-containing feed stream. This invention more particularly refers to a process for increasing yields of light weight olefins through cracking of heavier olefins produced in a methanol to olefins process.

BACKGROUND OF THE INVENTION

Light weight olefins have traditionally been produced through the process of steam or catalytic cracking. Because of the limited availability and high cost of petroleum sources, the cost of producing light weight olefins from such petroleum sources has been steadily increasing. Light weight olefins serve as feeds for the production of numerous chemicals. As the emerging economies of the Third World strain toward growth and expansion, the demand for light weight olefins will increase dramatically.

The search for alternative materials for light weight olefin production has led to the use of oxygenates such as alcohols and, more particularly, to the use of methanol, ethanol and higher alcohols or their derivatives. These alcohols may be produced by fermentation or from synthesis gas. Synthesis gas can be produced from natural gas, petroleum liquids and from carbonaceous materials including coal, recycled plastics, municipal wastes, or any organic material. Thus, alcohol and alcohol derivatives may provide non-petroleum based routes for the production of olefins and other hydrocarbons. Methanol, in particular, is useful in this process which is referred to herein as methanol to olefins (MTO).

Molecular sieve catalysts such as the microporous crystalline zeolite and non-zeolitic catalysts, particularly silicoaluminophosphates (SAPO), are known to promote the conversion of oxygenates to hydrocarbon mixtures. Numerous patents describe this process for various types of these catalysts: U.S. Pat. No. 3,928,483; U.S. Pat. No. 4,025,575; U.S. Pat. No. 4,052,479; U.S. Pat. No. 4,496,786; U.S. Pat. No. 4,547,616; U.S. Pat. No. 4,677,243; U.S. Pat. No. 4,843,183; U.S. Pat. No. 4,499,314; U.S. Pat. No. 4,447,669; U.S. Pat. No. 5,095,163; U.S. Pat. No. 5,191,141; U.S. Pat. No. 5,126,308; U.S. Pat. No. 4,973,792 and U.S. Pat. No. 4,861,938.

The process may be generally conducted in the presence of one or more diluents which may be present in the oxygenate-containing feed in an amount between about 1 and about 99 mol-%, based on the total number of moles of all feed and diluent components fed to the reaction zone (or catalyst). Diluents include, but are not limited to, helium, argon, nitrogen, carbon monoxide, carbon dioxide, hydrogen, water, paraffins, hydrocarbons (such as methane and the like), aromatic compounds, or mixtures thereof. U.S. Pat. No. 4,861,938 and U.S. Pat. No. 4,677,242 particularly emphasize the use of a diluent combined with the feed to the reaction zone to maintain sufficient catalyst selectivity toward the production of light weight olefin products, particularly ethylene. The above U.S. patents are hereby incorporated by reference in their entirety.

U.S. Pat. No. 5,026,935 discloses a process for the preparation of ethylene from $C_4$ or higher feed by the combination of cracking and metathesis to form ethylene and propylene and at least a portion of the propylene is metathesized to ethylene.

Generally, the ratio of ethylene/propylene on a carbon basis varies from about 0.1 to about 10 and, more typically, varies from about 0.8 to about 2.5. Ethylene and propylene are particularly desirable olefins but it has been found that their yields are reduced by the production of medium weight hydrocarbons such as $C_4$, $C_5$ and $C_6$ olefins, as well as some heavier components. Methods are needed to alter the product distribution in the MTO process for making light weight olefins to provide processing flexibility and overcome the equilibrium limitations of aluminophosphate catalysts in the MTO process. Methods are sought to reduce the production of $C_4$, $C_5$ and higher olefins from the MTO process relative to the production of ethylene and propylene. Such yield improvements of ethylene and propylene significantly improve the economies of the methanol to olefins process. A new improved process for conversion of oxygenates to hydrocarbons is provided by the present invention in the enhancement of production of ethylene and propylene.

SUMMARY OF THE INVENTION

In the present invention, a combination of a light weight olefin production process and a catalytic cracking process is employed to significantly increase the amount of desirable olefin products above the equilibrium amount provided by a molecular sieve catalyst. It was discovered that the use of this combination of an aliphatic hetero compound conversion process in a first reactor and a catalytic cracking reactor significantly increases the yield of the desired ethylene and propylene monomers. The catalytic cracking reactor employs the process of passing a $C_4$ and higher carbon feedstock through a reactor containing a crystalline silicate catalyst selected from an MFI-type crystalline silicate having a silicon/aluminum atomic ratio of at least 180 and an MEL-type crystalline silicate having a silicon/aluminum atomic ratio of from 150 to 800 which has been subjected to a steaming step, at an inlet temperature of from 450° C. to 600° C., at an olefin partial pressure of from 0.1 to 2 bars and the feedstock being passed over the catalyst at an LHSV of from 1 to 40 hr$^{-1}$ to produce an effluent with an olefin content of lower molecular weight than that of the feedstock, intermittently removing a first fraction of the catalyst from the reactor, regenerating the first fraction of the catalyst in a regeneration zone and intermittently feeding into the reactor a second fraction of the catalyst which has been regenerated in the regeneration zone, the catalyst regeneration rate being controlled whereby the propylene purity is maintained constant at a value corresponding to the average value observed in a reactor using the same feedstock, catalyst and cracking conditions, for example at least 94 wt-%. The reactor may be a fixed bed reactor with periodic regeneration by pressure swing regeneration or temperature swing regeneration or a moving bed reactor with continuous catalyst regeneration. The preferred SAPO catalysts are silicalite catalysts that have a Si/Al atomic molar ratio of 175 for unsteamed catalyst and 225 for steamed catalyst. The addition of the catalytic cracking reactor to the MTO reactor can typically raise the yield of ethylene plus propylene from about 77% without the catalytic cracking reactor to about 84% with the catalytic cracking reactor.

Accordingly, in one embodiment, the present invention relates to a process for the production of light weight olefins. The process comprises passing an olefin-rich feedstock comprising $C_2$ to $C_8$ olefins to a first stage separation zone to provide a light weight olefin stream comprising $C_2$ to $C_3$ olefins and a heavier olefin stream comprising $C_4^+$ olefins. The heavier olefin stream is passed to a second stage separation zone to provide a second light weight olefin stream, a medium weight olefin stream comprising $C_4$ to $C_7$ olefins, and a $C_7^+$ olefin stream. The medium weight olefin stream is passed to an olefin cracking reactor to convert at least a portion of the medium weight olefin stream into a cracked olefin stream comprising $C_2$ to $C_3$ olefins. At least a portion of the cracked olefin stream is returned to the second stage separation zone and a drag stream is withdrawn comprising the remaining portion of the cracked olefin stream. At least a portion of the second light weight olefin stream is returned to the first separation zone.

In another embodiment, the present invention relates to a process for increasing yield of ethylene and propylene from a methanol to olefins reactor. The process comprises sending a stream of medium weight olefins to an olefin cracking reactor. The medium weight olefins are contacted with an olefin cracking catalyst within the olefin cracking reactor to produce a mixture comprising ethylene, propylene, medium weight olefins, heavy weight olefins and other products. The mixture is separated into separate streams comprising at least one light weight olefin stream comprising one or more of ethylene and propylene, a medium weight stream comprising the medium weight olefins and other products and a heavy weight olefin stream.

In a further embodiment, the present invention relates to an integrated system for producing ethylene and propylene comprising at least one methanol to olefins reactor, at least one olefin cracking reactor, at least one line between the reactors for passage of reactor effluent from the methanol to olefins reactor and at least one separation zone for separating light weight olefins, medium weight olefins, heavy weight olefins and other products into separate streams.

In a preferred embodiment of the invention, the yield can be further improved through a recycle and purge operation to as high as about 90% on a carbon basis relative to the methanol feed to the MTO reactor.

The invention provides a process for the production of light weight olefins comprising ethylene and propylene from an oxygenate feedstock such as one or more alcohols or ethers or mixtures thereof. The process comprises passing an oxygenate-containing feedstock to a fluidized reaction zone in the presence of a diluent, the feedstock having from 1 to 4 carbon atoms per molecule. The first or fluidized reaction zone contains an aluminophosphate molecular sieve catalyst at conditions effective to convert the oxygenate-containing feedstock to a light weight olefin product stream comprising olefins comprising ethylene, propylene and butylene as well as some heavier products that are less desirable and to produce a spent aluminophosphate molecular sieve catalyst. The light weight olefin product stream is passed to a separation zone to separate the light weight olefin product stream into an ethylene stream, a propylene stream and a mixed butylene and heavier stream. The majority of the component of the product stream that comprises olefins higher than $C_6$ is purged from the system at this point. These higher carbon products may be used for purposes such as in preparation of gasoline or other fuels. At least a portion of the spent aluminophosphate molecular sieve catalyst is withdrawn from the fluidized reaction zone and the spent aluminophosphate molecular sieve catalyst is passed to a regeneration zone to be regenerated with an oxygen-containing stream. The regenerated catalyst is returned to the fluidized reaction zone. At least a portion of the mixed butylene and heavier stream ($C_4$ to $C_7$) is passed to a catalytic cracking reactor in which the mixed butylene and heavier stream passes through a reactor containing a crystalline aluminosilicate zeolitic catalyst selected from an MFI-type crystalline silicate having a silicon/aluminum atomic ratio of at least 180 and an MEL-type crystalline silicate having a silicon/aluminum atomic ratio of from 150 to 800 which has been subjected to a steaming step, at an inlet temperature of from 500° to 600° C., at an olefin partial pressure of from 0.1 to 2 bars with the feedstock being passed over the catalyst at an LHSV of from 5 to 30 $hr^{-1}$ to produce an effluent with an olefin content of lower molecular weight than that of the feedstock, intermittently removing a first fraction of the catalyst from the reactor, regenerating the first fraction of the catalyst in a regeneration zone and intermittently feeding into the moving bed reactor a second fraction of the catalyst which has been regenerated in the regeneration zone, the catalyst regeneration rate being controlled whereby the propylene purity is maintained constant at a value corresponding to the average value observed in a fixed bed reactor using the same feedstock, catalyst and cracking conditions, for example at least 94 wt-%.

DETAILED DESCRIPTION OF THE INVENTION

Figure 1:
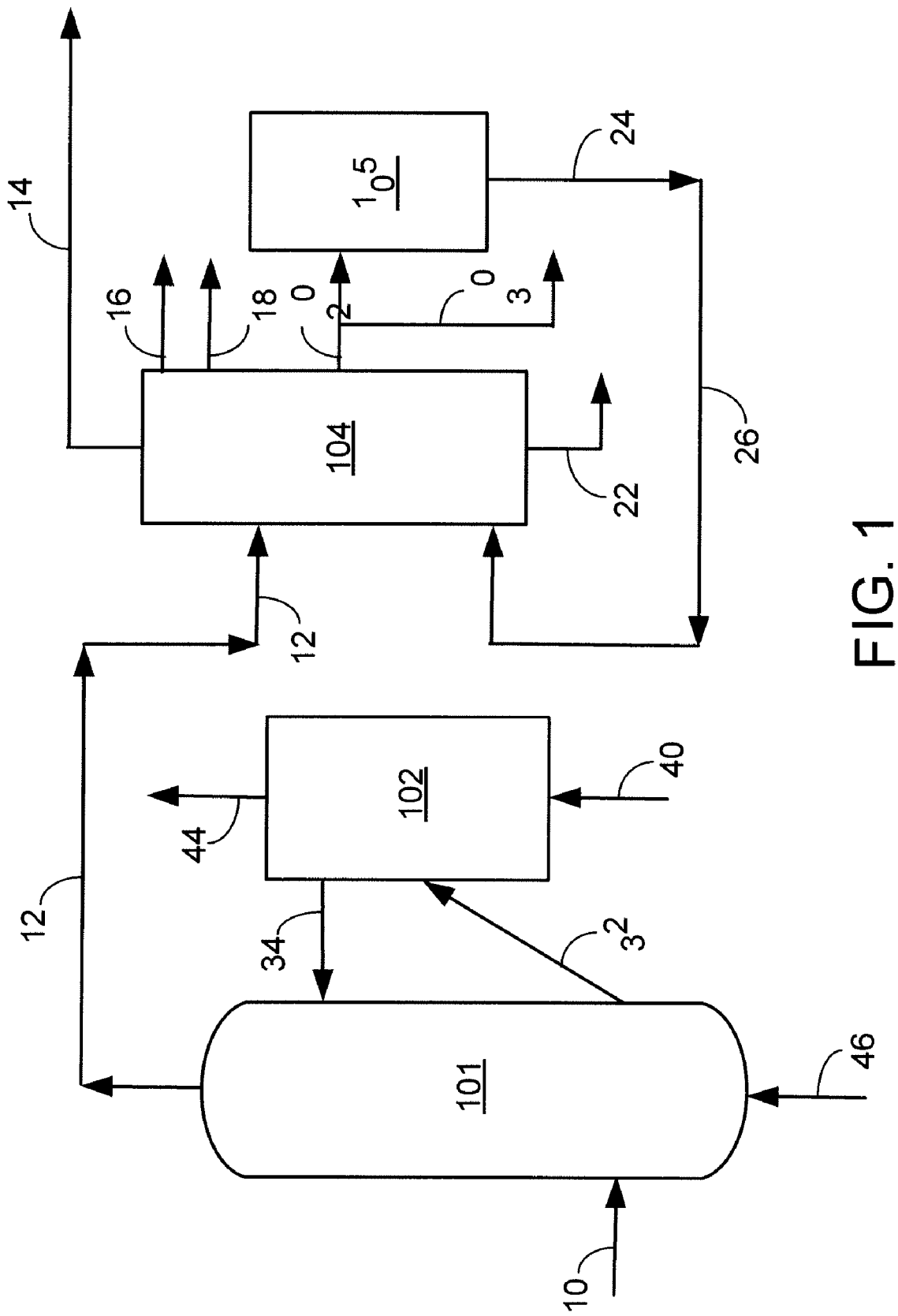
FIG. 1 is a schematic process flow diagram illustrating the process of the instant invention.

This invention comprises a process for the catalytic conversion of an oxygen-containing feedstock comprising one or more aliphatic hetero compounds comprising alcohols, halides, mercaptans, sulfides, amines, ethers and carbonyl compounds or mixtures thereof to a hydrocarbon product containing light weight olefinic products, i.e., $C_2$, $C_3$ and/or $C_4$ olefins. Alcohol feedstocks are particularly useful in the practice of this invention. The feedstock is contacted with a silicoaluminophosphate molecular sieve at effective process conditions to produce light weight olefins. Silicoaluminophosphate molecular sieves which produce light weight olefins are generally employable in the instant process. The preferred silicoaluminophosphates are those described in U.S. Pat. No. 4,440,871. Silicoaluminophosphate molecular sieves employable in the instant process are more fully described hereinafter. Increased yield of the light weight olefinic products is provided by sending $C_4$ to $C_7$ medium weight olefins to an olefin cracking reactor. Depending upon operating conditions, the medium weight olefins may be $C_4$ to $C_6$ olefins or $C_4$ to $C_5$ olefins.

The preferred process of the present invention employs an oxygenate feedstock. The term "oxygenate feedstock" is employed herein to include alcohols, ethers and carbonyl compounds (such as aldehydes, ketones and carboxylic acids). The oxygenate feedstock preferably contains from 1 to about 10 carbon atoms and, more preferably, contains from 1 to about 4 carbon atoms. Suitable oxygenates include lower straight or branched chain alkanols and their unsaturated counterparts. Representatives of suitable oxygenate feedstocks include methanol, dimethyl ether, ethanol, diethyl ether, methylethyl ether, formaldehyde, dimethyl ketone, acetic acid and mixtures thereof.

In accordance with the process of the present invention, an oxygenate feedstock is catalytically converted to hydrocarbons including aliphatic moieties such as, but not limited to, paraffins and olefins such as methane, ethane, ethylene, propane, propylene, butylene and limited amounts of other higher aliphatics by contacting the oxygenate feedstock with a preselected catalyst. The total charge of oxygenate feedstock to the aliphatic conversion reaction zone may contain additional compounds such as diluents. The invention will be hereinafter discussed further with reference to oxygenates and an oxygenate conversion process.

A diluent is preferred to be present to maintain the selectivity of the catalyst to produce light weight olefins, particularly ethylene and propylene. Examples of diluents which may be used are helium, argon, nitrogen, carbon monoxide, carbon dioxide, hydrogen, steam, paraffinic hydrocarbons, aromatic hydrocarbons (e.g., benzene and toluene) and mixtures thereof. The amount of diluent used can vary considerably and is usually from about 5 to about 90 mol-% of the feedstock and preferably from about 10 to about 50 mol-%. The use of steam as the diluent provides certain equipment cost and thermal efficiency advantages. The phase change between steam and liquid water can be employed to advantage in transferring heat between the feedstock and the reactor effluent and the separation of the diluent from the product requires simple condensation of the water to separate the water from the hydrocarbons. Ratios of 1 mole of feed to about 0.1 to 5 moles of water are typical.

The oxygenate conversion process of the present invention is preferably conducted in the vapor phase such that the oxygenate feedstock is contacted in a vapor phase in a reaction zone with a molecular sieve catalyst at effective process conditions to produce hydrocarbons, at effective temperatures, pressures and WHSV and, optionally, an effective amount of diluent, correlated to produce the desired yield of light weight olefin products. The process is conducted for a period of time sufficient to produce the desired light weight olefin products. In general, the residence time employed to produce the desired product can vary from seconds to a number of hours. It will be readily appreciated that the residence time will be determined to a significant extent by the reaction temperature, the molecular sieve selected, the WHSV, the phase (liquid or vapor) and process design characteristics selected. The feedstock flow rate affects olefin production. Increasing the feedstock flow rate (expressed as weight hourly space velocity, or WHSV) enhances olefin production relative to paraffin production. However, the enhanced olefin production relative to paraffin production is offset by a diminished conversion of oxygenate to hydrocarbons.

The oxygenate conversion process is effectively carried out over a wide range of pressures, including autogenous pressures. At pressures between about 0.001 atmospheres (0.76 torr) and about 1000 atmospheres (760,000 torr), the formation of light weight olefin products will be effected, although the optimum amount of product will not necessarily form at all pressures. The preferred pressure is between about 0.01 atmospheres (7.6 torr) and about 100 atmospheres (76,000 torr). More preferably, the pressure will range from about 1 to about 10 atmospheres. The pressures referred to herein for the process are exclusive of the inert diluent, if any, that is present and refer to the partial pressure of the feedstock as it relates to oxygenate compounds and/or mixtures thereof. Pressures outside the stated range are not excluded from the scope of this invention, although such do not fall within certain desirable embodiments of the invention. At the lower and upper end of the pressure range and beyond, the selectivities, conversions and/or rates to light weight olefin products may not occur at the optimum, although light weight olefin such as ethylene may still be formed.

The temperatures which may be employed in the oxygenate conversion process may vary over a wide range depending, at least in part, on the selected molecular sieve catalyst. In general, the process can be conducted at an effective temperature between about 300° and about 600° C. Temperatures outside the stated range are not excluded, although they do not fall within certain desirable embodiments of the present invention. At the lower end of the temperature range and thus, generally at a lower rate of reaction, the formation of the desired light weight olefin products may become markedly slow. At the upper end of the temperature range and beyond, the process may not form an optimum amount of light weight olefin products and catalyst deactivation may be rapid. Notwithstanding these factors, the reaction will still occur and the feedstock, at least in part, can be converted to the desired light weight olefin products at temperatures outside the range between about 200° and about 700° C.

In the oxygenate conversion process wherein aliphatic hetero compounds are converted into light weight olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably, by adsorption of n-hexane (average kinetic diameter of about 0.43 nm) and negligible adsorption of isobutane. Negligible adsorption of a given adsorbate is adsorption of less than 3 wt-% of the catalyst and adsorption of the adsorbate is over 3 wt-% of the adsorbate based on the weight of the catalyst. Certain of the catalysts useful in the present invention have pores with an average effective diameter of less than 5 angstroms. The average effective diameter of the pores of preferred catalysts is determined by measurements described in D. W. Breck, ZEOLITE MOLECULAR SIEVES, 1984, Robert E. Krieger Publishing Company, Florida (pp. 425-438), hereby incorporated by reference in its entirety. The term "effective diameter" is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves and non-zeolitic molecular sieves.

Zeolitic molecular sieves in the calcined form may be represented by the general formula:

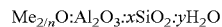

$$Me_{2/n}O:Al_2O_3:xSiO_2:yH_2O$$

where Me is a cation, x has a value from about 2 to infinity, n is the cation valence and y has a value of from about 2 to 10.

Typically, well-known zeolites which may be used include chabazite—also referred to as Zeolite D, clinoptilolite, erionite, faujasite—also referred to as Zeolite X and Zeolite Y, ferrierite, mordenite, Zeolite A, Zeolite P, ZSM-5, ZSM-11 and MCM-22. Other zeolites include those having a high silica content, i.e., those having silica/alumina ratios greater than 10 and typically greater than 100 can also be used. One such high silica zeolite is silicalite, as the term used herein includes both the silicapolymorph disclosed in U.S. Pat. No. 4,061,724 and also the F-silicate disclosed in U.S. Pat. No.

4,073,865, hereby incorporated by reference. Detailed descriptions of some of the above-identified zeolites may be found in D. W. Breck, supra.

Non-zeolitic molecular sieves include molecular sieves which have the proper effective pore size and are embraced by an empirical chemical composition, on an anhydrous basis, expressed by the empirical formula:

$$(EL_xAl_yP_z)O_2$$

where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01 and x+y+z=1. When EL is a mixture of metals, x represents the total amount of the element mixture present. Preferred elements (EL) are silicon, magnesium and cobalt, with silicon being especially preferred. These non-zeolitic molecular sieves are referred to as "ELAPOs" hereinafter.

The preparation of various ELAPOs are well known in the art and may be found in U.S. Pat. No. 5,191,141; U.S. Pat. No. 4,554,143; U.S. Pat. No. 4,440,871; U.S. Pat. No. 4,853,197; U.S. Pat. No. 4,793,984; U.S. Pat. No. 4,752,651 and U.S. Pat. No. 4,310,440; all of which are incorporated by reference. Generally, the ELAPO molecular sieves are synthesized by hydrothermal crystallization from a reaction mixture containing reactive sources of EL, aluminum, phosphorus and a templating agent. Reactive sources of EL are the metal salts such as the chloride and nitrate salts. When EL is silicon, a preferred source is fumed, colloidal or precipitated silica. Preferred reactive sources of aluminum and phosphorus are pseudo-boehmite alumina and phosphoric acid. Preferred templating agents are amines and quaternary ammonium compounds. An especially preferred templating agent is tetraethylammonium hydroxide (TEAOH).

A preferred embodiment of the process is one in which the element (EL) content varies from about 0.005 to about 0.05 mole fraction. If EL is more than one element, then the total concentration of all the elements is between about 0.005 and 0.05 mole fraction. An especially preferred embodiment is one in which EL is silicon (usually referred to silicoaluminophosphate or in short as SAPO). The SAPOs which can be used in the instant invention are any of those described in U.S. Pat. No. 4,440,871; U.S. Pat. No. 5,126,308 and U.S. Pat. No. 5,191,141. Of the specific crystallographic structures described in the '871 patent, the SAPO-34, i.e., structure type 34, is preferred. The SAPO-34 structure is characterized in that it adsorbs xenon but does not adsorb isobutane, indicating that it has a pore opening of about 4.2 angstroms. Another SAPO, SAPO-17, as exemplified in Examples 25 and 26 of the '871 patent, is also preferred. The SAPO-17 structure is characterized in that it adsorbs oxygen, hexane and water but does not adsorb isobutane, indicating that it has a pore opening of greater than about 4.3 angstroms and less than about 5.0 angstroms.

The preferred oxygenate conversion catalyst preferably is incorporated into solid particles in which the catalyst is present in an amount effective to promote the desired hydrocarbon conversion. In one embodiment of the invention, the solid particles comprise a catalytically effective amount of the catalyst and at least one matrix material, preferably selected from the group consisting of binder materials, filler materials and mixtures thereof to provide a desired property or properties, such as, desired catalyst dilution, mechanical strength to the solid particles. Such matrix materials are often, to some extent, porous in nature and may or may not be effective to promote the desired hydrocarbon conversion. The matrix materials may promote conversion of the feed stream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates and mixtures of two or more of these materials.

If matrix materials such as binder and/or filler materials are included in the catalyst composition, the non-zeolitic and/or zeolitic molecular sieves preferably comprise about 1 to 99 percent, more preferably about 5 to about 90 percent and still more preferably about 10 to about 80 percent, by weight of the total composition. The preparation of solid particles comprising catalyst and matrix materials is conventional and well known in the art and, therefore, need not be discussed in detail herein.

During the oxygenate conversion reaction, a carbonaceous material, i.e., coke, is deposited on the catalyst. The carbonaceous deposit material has the effect of reducing the number of active sites on the catalyst which thereby affects the extent of the conversion. During the conversion process, a portion of the coked catalyst is withdrawn from the reaction zone and regenerated to remove at least a portion of the carbonaceous material and returned to the oxygenate conversion reaction zone. Depending upon the particular catalyst and conversion, it can be desirable to substantially remove the carbonaceous material e.g., to less than 1 wt-%, or only partially regenerate the catalyst, e.g., to from about 2 to 30 wt-% carbon. Preferably, the regenerated catalyst will contain about 0 to 20 wt-% and more preferably from about 0 to 10 wt-% carbon. Additionally, during regeneration there may be oxidation of sulfur and in some instances nitrogen compounds along with the removal of metal materials from the catalyst. Moreover, regeneration conditions can be varied depending upon the catalyst used and the type of contaminant material present upon the catalyst prior to its regeneration. The details concerning the conditions for regeneration are known to those skilled in the art and therefore need not be further disclosed herein.

It was discovered that the butene and heavier material produced in the oxygenate conversion zone can be converted in a separate reactor, also called an "olefin cracking reactor" herein, to produce additional amounts of ethylene and propylene. The catalysts found to produce this conversion comprises a crystalline silicate of the MFI family which may be a zeolite, a silicalite or any other silicate in that family or the MEL family which may be a zeolite or any other silicate in that family. Examples of MFI silicates are ZSM-5 and silicalite. An example of an MEL zeolite is ZSM-11 which is known in the art. Other examples are Boralite D and silicalite-2 as described by the International Zeolite Association (Atlas of Zeolite Structure Types, 1987, Butterworths). The preferred crystalline silicates have pores or channels defined by ten oxygen rings and a high silicon/aluminum atomic ratio.

Crystalline silicates are microporous crystalline inorganic polymers based on a framework of $XO_4$ tetrahydra linked to each other by sharing of oxygen ions, where X may be trivalent (e.g. Al, B . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]: 0.51-0.55 nm. Crystalline silicates with the MEL structure possess a bi-directional intersecting straight pore system with straight channels along [100] having pore diameters of 0.53-0.54 nm.

The crystalline silicate catalyst has structural and chemical properties and is employed under particular reaction conditions whereby the catalytic cracking of the $C_4$ to $C_7$ olefins readily proceeds. Different reaction pathways can occur on the catalyst. Under the process conditions, having an inlet temperature of around 400° to 600° C., preferably from 520° to 600° C., yet more preferably 540° to 580° C., and an olefin partial pressure of from 0.1 to 2 bars, most preferably around atmospheric pressure. Furthermore, such isomerization tends to reach a thermodynamic equilibrium. Olefinic catalytic cracking may be understood to comprise a process yielding shorter molecules via bond breakage.

With such high silicon/aluminum ratio in the crystalline silicate catalyst, a stable olefin conversion can be achieved with a high propylene yield on an olefin basis of from 20 to 50% whatever the origin and composition of the olefinic feedstock. The total yield of $C_2$ and $C_3$ is thereby increased by up to 10% based upon the original feed volume.

The MFI catalyst having a high silicon/aluminum atomic ratio for use in the catalytic olefin cracking process of the present invention may be manufactured by removing aluminum from a commercially available crystalline silicate. A typical commercially available silicalite has a silicon/aluminum atomic ratio of around 120. The commercially available MFI crystalline silicate may be modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate framework structure to form alumina particles, those particles cause partial obstruction of the pores or channels in the framework. This inhibits the olefinic cracking processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst and thereby reduces the occurrence of hydrogen transfer reactions in the cracking process. The reduction of acidity ideally occurs substantially homogeneously throughout the pores defined in the crystalline silicate framework. This is because in the olefin-cracking process hydrocarbon species can enter deeply into the pores. Accordingly, the reduction of acidity and thus the reduction in hydrogen transfer reactions which would reduce the stability of the MFI catalyst are pursued throughout the whole pore structure in the framework. The framework silicon/aluminum ratio may be increased by this process to a value of at least about 180, preferably from about 180 to 1000, more preferably at least 200, yet more preferably at least 300 and most preferably around 480.

The MEL or MFI crystalline silicate catalyst may be mixed with a binder, preferably an inorganic binder, and shaped to a desired shape, e.g. extruded pellets. The binder is selected so as to be resistant to the temperature and other conditions employed in the catalyst manufacturing process and in the subsequent catalytic cracking process for the olefins. The binder is an inorganic material selected from clays, silica, metal oxides such as $ZrO_2$ and/or metals, or gels including mixtures of silica and metal oxides. The binder is preferably alumina-free, although aluminum in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica or $AlPO_4$.

The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst may be formulated into pellets, spheres, extruded into other shapes, or formed into a spray-dried powder. In the catalytic cracking process, the process conditions are selected in order to provide high selectivity towards propylene or ethylene, as desired, a stable olefin conversion over time, and a stable olefinic product distribution in the effluent. Such objectives are favored by the use of a low acid density in the catalyst (i.e. a high Si/Al atomic ratio) in conjunction with a low pressure, a high inlet temperature and a short contact time, all of which process parameters are interrelated and provide an overall cumulative effect. The process conditions are selected to disfavor hydrogen transfer reactions leading to the formation of paraffins, aromatics and coke precursors. The process operating conditions thus employ a high space velocity, a low pressure and a high reaction temperature. The LHSV ranges from 5 to 30 $hr^{-1}$, preferably from 10 to 30 $hr^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The hydrocarbon feedstocks are preferably fed at a total inlet pressure sufficient to convey the feedstocks through the reactor. The hydrocarbon feedstocks may be fed undiluted or diluted in an inert gas, e.g. nitrogen or steam. Preferably, the total absolute pressure in the reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° to 590° C., typically around 560° to 585° C.

In order to maximize the amount of ethylene and propylene and to minimize the production of methane produced from the butylene and heavier stream, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

A portion of the butylene and heavier stream, when cracked, will be converted to paraffinic compounds such as methane, ethane, propane, and heavier hydrocarbons. Unless at least a portion of these compounds is removed, coke will build up in the system. Therefore, a drag stream comprising $C_4$ and heavier hydrocarbons is removed from the process and used for plant fuel or blended into other hydrocarbon products such as motor gasoline.

The specified combination of the conversion of the feedstock to a mixture of light weight olefins at conditions favoring the production of these components coupled with the use of the thus formed butylene and heavier olefins to produce further quantities of product ethylene and propylene provides a synergistic combination of oxygenate conversion and cracking reaction steps whereby there are obtained substantially improved overall yields of the desired light weight olefins: ethylene and propylene.

DETAILED DESCRIPTION OF THE DRAWINGS

The following description of the present process is made with reference to the drawing. In the interest of simplifying the description of the invention, the process system in the drawing does not contain the several conduits, valves, heat exchangers, and the like which, in actual practice, would be provided in accordance with routine skill in the art to enable the process to be carried out on a continuous basis.

FIG. 1 illustrates the operation of the instant invention. An oxygenate feedstock in a line 10 comprising an alcohol and/or an ether having about 1 to about 4 carbon atoms per molecule is passed to a fluidized reaction zone 101. In the fluidized reaction zone 101, the oxygenate feedstock contacts a silicoaluminophosphate catalyst, optionally in the presence of a diluent which is shown as being introduced via a line 46. The fluidized reaction zone 101 is operated at a fluid reaction pressure and a fluid reaction temperature which is effective to convert the oxygenate feedstock to produce a light weight olefin product stream which is withdrawn in a line 12 and passed to a separation zone 104. In the separation zone 104, the light weight olefin product stream is separated by fractionation to provide a fuel gas stream in a line 14, an ethylene stream in a line 16, a propylene stream in a line 18, and a medium weight olefin stream comprising mixed butylene and heavier olefins in a line 20. A still heavier stream ($C_8$+) is removed through a line 22. Under some operating conditions, this still heavier stream is $C_6$+ or $C_7$+. The medium weight stream comprises $C_4$ to $C_7$ olefins, but under some operating conditions, may be $C_4$ to $C_6$ or $C_4$ to $C_5$ olefins. As the reaction takes place in the fluidized reaction zone 101, a portion of the catalyst is deactivated by the build-up of coke on the catalyst to produce a spent catalyst. A portion of the spent catalyst is conveyed to a regeneration zone 102 via a catalyst transfer line 32. In the regeneration zone 102, the spent catalyst is contacted with an oxygen-containing stream such as air or oxygen introduced in a line 40 to at least partially reduce the build-up of coke on the spent catalyst and to produce a regenerated catalyst having a reduced amount of coke relative to spent catalyst. During the regeneration, carbon oxides are produced which are removed from the regeneration zone 102 via a line 44. Preferably, spent catalyst comprises from about 3 to about 15 wt-% coke and the regenerated catalyst comprise about 1 to about 5 wt-% coke. A first portion of the regenerated catalyst is returned to the fluidized reaction zone 101 via a line 34. At least a portion of the mixed butylene and heavier stream is passed to an olefin cracking reactor 105 via the line 20. In the olefin cracking reactor 105, at conditions effective for the conversion, the mixed butylene and heavier stream is converted or cracked to provide to a second product stream comprising additional amounts of ethylene and propylene. Preferably, the olefin cracking reactor 105 is maintained at a secondary reactor temperature of between about 450° and about 600° C. and a pressure ranging from about 100 kPa (15 psia) to about 450 kPa (65 psia) to obtain the desired conversion of the butylene and higher carbons. More preferably, the temperature of the olefin cracking reactor 105 ranges between about 540° and about 590° C. The reaction may be carried out in the presence of a second diluent such as steam, nitrogen, methane, etc. The lighter product stream is sent through lines 24 and 26 back to the separation zone 104. A small portion of the stream in the line 20 is purged through a line 30. Because the $C_4$ to $C_7$ olefinic stream that is being recycled contains some paraffins and small amounts of such paraffins are formed in the olefin cracking reactor, it is advisable to maintain a small purge through the line 30 in order to avoid the build-up of such paraffins. This purge may also be removed from the stream returning from the olefin cracking reactor 105 to the separation zone 104. Thus, the output of the fluidized reaction zone 101 is coupled to an input of the separation zone 104 and an output of the olefin cracking reactor 105 is coupled to a separate input of the separation zone 104. The olefin cracking reactor is after the fluidized reaction zone 101, after a regeneration zone 102, and after the separation zone 104.

The embodiment of the invention shown in FIG. 1 recycles the product to the separation zone 104 for separation of the olefins. The light weight olefins and the medium weight $C_4$ to $C_7$ olefins pass back through the olefin cracking reactor and the $C_8$ and higher olefins are removed from the system.

Figure 2:
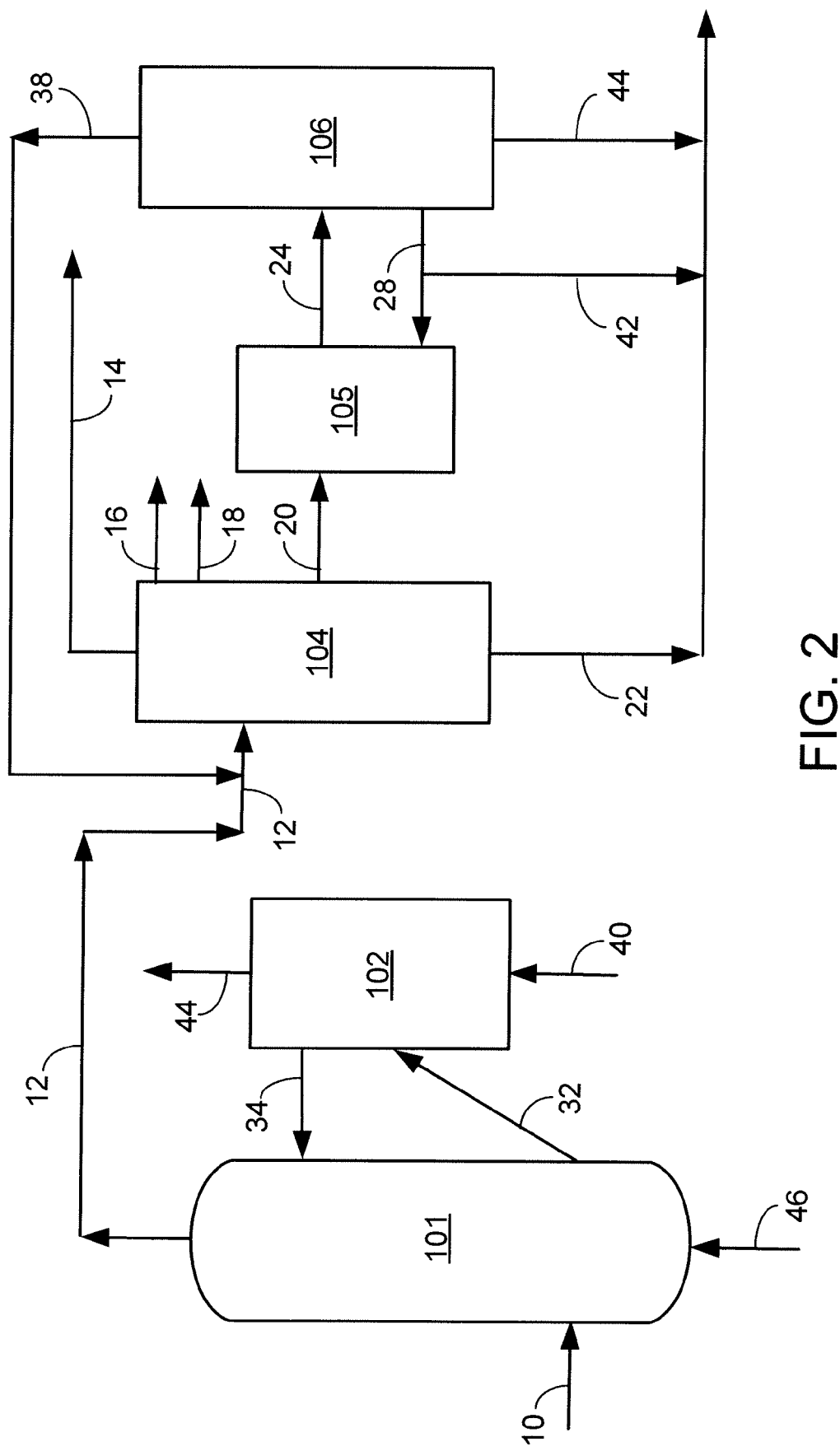
FIG. 2 shows a separation unit added to the schematic process of FIG. 1.

An alternative embodiment is shown in FIG. 2 with a second separation zone 106 shown after the olefin cracking reactor 105. The features of FIG. 2 are the same as FIG. 1, except as explained hereinafter. The line 24 is shown passing the effluent from the olefin cracking reactor 105 to this second separation zone 106. A stream of light weight olefins $C_3$ and lower is shown in a line 38 from the top of the second separation zone 106 to be sent to be returned to the line 12 to be separated further in the separation zone 104. A line 28 takes the medium weight $C_4$ to $C_7$ fraction to be returned to the olefin cracking reactor 105. The line 22 takes the rejected heavy $C_6{}^+$ to be utilized outside the process of the present invention, such as to be mixed into a gasoline blending stream. A small portion of the $C_4$ to $C_7$ steam (typically about 1-5%) is purged through a line 42 to prevent build up of paraffins in the system and the subsequent build up of coke. The line 42 purge as shown connects to the line 22 to be part of the heavy weight olefin stream exiting the system or the purge may be placed in accordance with the knowledge of one skilled in the art. Also connecting to the line 22 is the line 44, through which pass rejected heavy $C_8$ from the second separation zone 106. As noted above, throughout the process, the medium weight olefin stream may be $C_4$ to $C_7$, $C_4$ to $C_6$ or $C_5$ to $C_6$ olefins depending upon the operating conditions. The heavy weight olefin stream that is rejected may be $C_8^+$, $C_7^+$ or $C_6^+$ depending upon said operating conditions.

The following example is only used to illustrate the present invention and is not meant to be limiting.

EXAMPLE

The process of the present invention was tested and the combined carbon yield of $C_2$ plus $C_3$ was increased from 77.6% without the olefin cracking to 88.7% with the use of the olefin cracking unit. The amount of $C_4^+$ purged decreased from about 17.0% to about 4.5% by weight of the stream. This is considered to be a very significant increase in yield.

The invention claimed is:

1. An integrated system for producing ethylene and propylene comprising at least one methanol to olefins reactor, at least one olefin cracking reactor, at least one line between said reactors for passage of reactor effluent from said methanol to olefins reactor and at least one separation zone for separating light weight olefins, medium weight olefins, heavy weight olefins and other products into separate streams, an output of the at least one methanol to olefins reactor coupled to an input of the at least one separation zone and an output of the at least one olefin cracking reactor coupled to a separate input of the at least one separation zone.

2. The integrated system of claim 1 wherein said light weight olefins comprise ethylene and propylene, said medium weight olefins comprise $C_4$ to $C_7$ olefins and said heavy weight olefins comprise $C_8$ and higher olefins.

3. The integrated system of claim 1 wherein said light weight olefins comprise ethylene and propylene, said medium weight olefins comprise $C_4$ to $C_6$ olefins and said heavy weight olefins comprise $C_7$ and higher weight olefins.

4. The integrated system of claim 1 wherein said light weight olefins comprise ethylene and propylene, said medium weight olefins comprise $C_4$ to $C_5$ olefins and said heavy weight olefins comprise $C_6$ and higher weight olefins.

5. The integrated system of claim 1 wherein said medium weight olefins are sent to said olefin cracking reactor in which said medium weight olefins are contacted with an olefin cracking catalyst to convert some of said medium weight olefins to light weight olefins.

6. The integrated system of claim 1 wherein a sufficient portion of said medium weight olefins are purged from said system to prevent build up of paraffins within said integrated system.

7. An integrated system for producing ethylene and propylene comprising at least one methanol to olefins reactor, at least one olefin cracking reactor, at least one line between said reactors for passage of reactor effluent from said methanol to olefins reactor and at least one separation zone for separating light weight olefins, medium weight olefins, heavy weight olefins and other products into separate streams, the at least one olefin cracking reactor after the at least one methanol to olefins reactor, after a regeneration zone, and after at least one separation zone.

8. The integrated system of claim 7, wherein said medium weight olefins are sent to said at least one olefin cracking reactor in which said medium weight olefins are contacted with an olefin cracking catalyst to convert some of said medium weight olefins to light weight olefins, said olefin cracking catalyst different from a methanol to olefins catalyst contained in said at least one methanol to olefins reactor.

* * * * *